(12) United States Patent
Guo et al.

(10) Patent No.: US 11,957,752 B2
(45) Date of Patent: Apr. 16, 2024

(54) NEAR-INFRARED NANO-PHOTOSENSITIZER, AND PREPARATION METHOD AND USE THEREOF

(71) Applicant: SOOCHOW UNIVERSITY, Suzhou (CN)

(72) Inventors: Zhengqing Guo, Suzhou (CN); Hui He, Suzhou (CN); Mengke Shi, Suzhou (CN); Han Xu, Suzhou (CN); Dandan Ji, Suzhou (CN); Yangyang Huang, Suzhou (CN); Qiujin He, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 0 days.

(21) Appl. No.: 18/026,250

(22) PCT Filed: Jan. 25, 2022

(86) PCT No.: PCT/CN2022/073615
§ 371 (c)(1),
(2) Date: Mar. 14, 2023

(87) PCT Pub. No.: WO2023/133937
PCT Pub. Date: Jul. 20, 2023

(65) Prior Publication Data
US 2023/0390395 A1    Dec. 7, 2023

(30) Foreign Application Priority Data
Jan. 11, 2022    (CN) .......................... 202210025998.5

(51) Int. Cl.
*A61K 41/00* (2020.01)
*A61K 9/10* (2006.01)
*A61K 9/107* (2006.01)

(52) U.S. Cl.
CPC ........ *A61K 41/0057* (2013.01); *A61K 9/1075* (2013.01)

(58) Field of Classification Search
CPC .......................... A61K 41/0057; A61K 9/1075
See application file for complete search history.

(56) References Cited

FOREIGN PATENT DOCUMENTS

| CN | 105833271 A |   | 8/2016 |              |
|----|-------------|---|--------|--------------|
| CN | 109078185 A | * | 12/2018 | ......... A61K 41/0057 |
| CN | 109078185 A |   | 12/2018 |              |
| CN | 110003461 A |   | 7/2019 |              |
| CN | 112920210 A |   | 6/2021 |              |

OTHER PUBLICATIONS

CN109078185A, Machine Translation (Year: 2018).*
Zhengqing Guo et al., "Heavy-Atom-Modulated Supramolecular Assembly Increases Antitumor Potency against Malignant Breast Tumors via Tunable Cooperativity" Adv. Mater. vol. 33, No. 2 pp. 1-15 (Dec. 3, 2020).
Sundus Erbas et al. "Non-covalent functionalized SWNTs as delivery agents for novel Bodipy-based potential PDT sensitizers" Chem. Commum. No. 33, pp. 4956-4957 (Dec. 31, 2009).

* cited by examiner

Primary Examiner — Jeffrey S Lundgren
Assistant Examiner — Ibrahim D Bori
(74) Attorney, Agent, or Firm — SZDC Law PC

(57) ABSTRACT

The present invention relates to the technical field of photosensitizers, and particularly to a near-infrared nano-photosensitizer and a preparation method and use thereof. The near-infrared nano-photosensitizer in the present invention is modified by conjugation extension of the boron dipyrromethene core, achieving absorption and emission spectra close to the near-infrared region. A polyfluoroalkyl group and a polyethylene glycol group are introduced to the boron dipyrromethene structure to obtain an amphiphilic photosensitizer. By means of the strong fluorine-fluorine interaction between the polyfluoroalkyl group and the hydrophilic interaction of the polyethylene glycol group, a nano-photosensitive micelle with an ultra-low CMC value is ultimately constructed. Boron dipyrromethene is induced by fluorine-fluorine interaction to undergo J-aggregation, causing the maximum absorption peak to red-shift to the near-infrared region, beneficial to the deep phototherapy of tumors.

10 Claims, 8 Drawing Sheets

NEAR-INFRARED NANO-PHOTOSENSITIZER, AND PREPARATION METHOD AND USE THEREOF

This application is the National Stage Application of PCT/CN2022/073615, filed on Jan. 25, 2022, which claims priority to Chinese Patent Application No. 202210025998.5, filed on Jan. 11, 2022, which is incorporated by reference for all purposes as if fully set forth herein.

FIELD OF THE INVENTION

The present invention relates to the technical field of photosensitizers, and particularly to a near-infrared nano-photosensitizer and a preparation method and use thereof.

DESCRIPTION OF THE RELATED ART

Tumor is a neoplasm formed due to local tissue cell proliferation in an organism in the presence of various tumorigenic factors. The development of new tumor treatments is an important direction in the current medical field. In recent years, with the development and use of laser technology, photodynamic therapy has gradually become a tumor treatment. As a core element in photodynamic therapy, photosensitizers can transfer the energy of excitation light to oxygen in the tissue, convert it into reactive oxygen species (such as singlet oxygen), and oxidize lipids and endogenous molecules such as proteins and nucleic acids, causing irreversible tissue damage. However, most photosensitizers generally have poor photostability, poor water solubility, low performance of targeting, low treatment depth and other defects. These severely limit the use of photodynamic therapy in clinics.

Critical micelle concentration (CMC), as a performance parameter, plays an important role in describing the stability of nanomicelles or vesicles. In photosensitive drug delivery, conventional nanomicelles are often diluted to below the critical micelle concentration by the body fluids, and the nanomicelles are depolymerized in advance to release the photosensitive drug, causing limited enrichment of the photosensitive drug at the tumor site. Also, most photosensitizers, such as porphyrin, chlorin, fused quinones, and other compounds, have maximum absorption peaks in the ultraviolet and visible bands. Light in these bands can be absorbed by hemoglobin, melanin and other pigment-containing proteins in the body, making it impossible to reach the interior of the tumor tissue. Therefore, the design and synthesis of near-infrared nano-photosensitive micelles with ultra-low critical micelle concentration is an important problem to be solved in the field of photodynamic therapy.

Chinese Patent No. CN109078185A discloses a method for assembling a high-efficiency nano-photosensitizer, by introducing a long-chain alkyl group and a polyethylene glycol segment of appropriate length to construct an amphiphilic photosensitive molecule. However, two problems have not been solved in this patent yet. One is the failure to construct a photosensitive micelle with a lower CMC value, leading to poor stability. The second is that the maximum absorption peak of the prepared photosensitive micelle cannot be red-shifted to the near-infrared region, making it impossible to reach the interior of the tumor tissue.

Due to the smaller atomic radius and the strongest electronegativity of the fluorine atom, the introduction of fluorine atoms often brings unexpected physical and chemical properties, so it is widely used in material science, atomic energy, aerospace and other areas. In recent years, the use of fluorine-containing compounds in the field of biomedicine has attracted much attention, such as fluorine-containing drugs, fluorine-containing anesthetics, fluorine-containing tracers, and drug carriers, etc. The "fluorophilic" interaction between polyfluoroalkyl groups can be used in biological detection, solid-phase separation, homogeneous catalysis, label synthesis and other fields. In addition to the above fields, fluorine . . . fluorine interaction can also be used for efficient self-assembly of nanostructures, for example, self-assembled gold fluoride nanoparticles, fluorinated DNA micelles, and fluorinated nanodroplets, etc.

The deficiencies existing in the prior art mainly include: (1) Although the existing photosensitizers have achieved certain therapeutic effects in clinic, they still have poor tissue targeting, poor photostability, insufficient treatment depth, long-term phototoxicity caused by slow metabolism, and other problems. (2) Boron dipyrromethene is a new type of organic dye molecule, having strong molar extinction coefficient, high fluorescence quantum yield and other advantages. The radiative transition rate and intersystem crossing probability of boron dipyrromethene can be regulated by different strategies to obtain a long-lived triplet excited state. However, its maximum absorption peak is often in the visible region. Limiting the use of such compounds in phototherapy. (3) Although polymers, human serum albumin, and inorganic nanomaterials are used as delivery vehicles to improve the water solubility, photostability and targeting performance of the photosensitizer. After injection into the body, such nano-photosensitizers are often considered unstable. Therefore, the development of new photosensitizer drugs still faces great challenges.

SUMMARY OF THE INVENTION

To this end, the technical problem to be solved by the present invention is to overcome the problem of poor photostability and low treatment depth in the prior art.

To solve the above technical problems, the present invention provides a near-infrared nano-photosensitizer and a preparation method and use thereof.

A first object of the present invention is to provide a near-infrared nano-photosensitizer, having a structure of Formula (I):

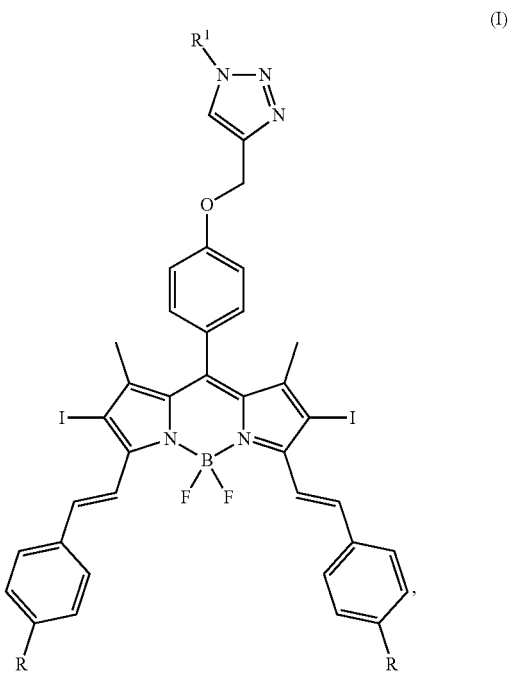

wherein R is

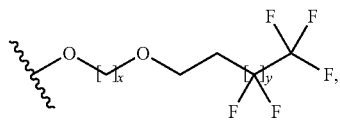 [SMILES: *OCOCCC(F)(F)C(F)(F)F]

x+y=11, x and y are both a positive integer;
R¹ is

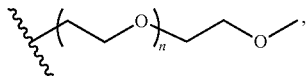

n=11-227, and n is a positive integer.

In an embodiment of the present invention, y is 3, 5 or 7.

A second object of the present invention is to provide a method for preparing a near-infrared nano-photosensitizer, which comprises the following steps:

(1) Reacting a compound of Formula (II) with

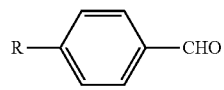

in the presence of acetic acid and piperidine in a solvent, to obtain a compound of Formula (III); and (2) Reacting the compound of Formula (III) obtained in Step (1) with azido functionalized polyethylene glycol in the presence of copper sulfate pentahydrate and sodium ascorbate in a solvent, to obtain a compound of Formula (I).

The structures of Formulas (I), (II) and (III) are shown below:

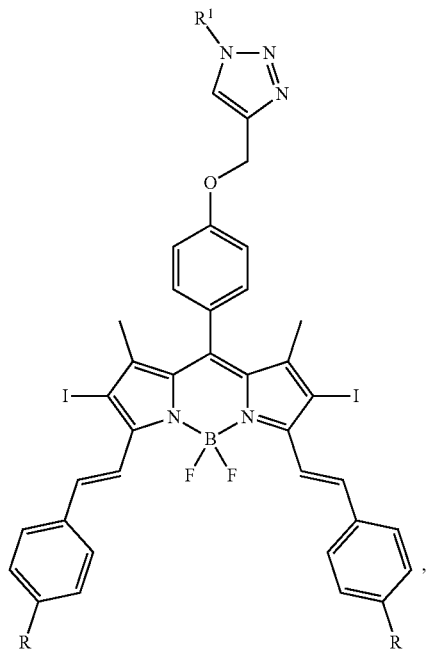

(I)

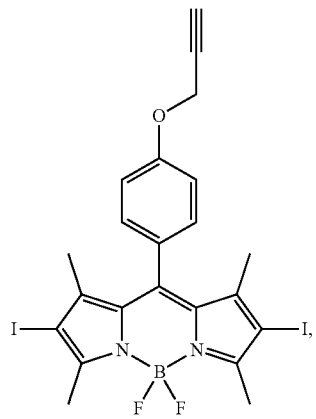

(II)

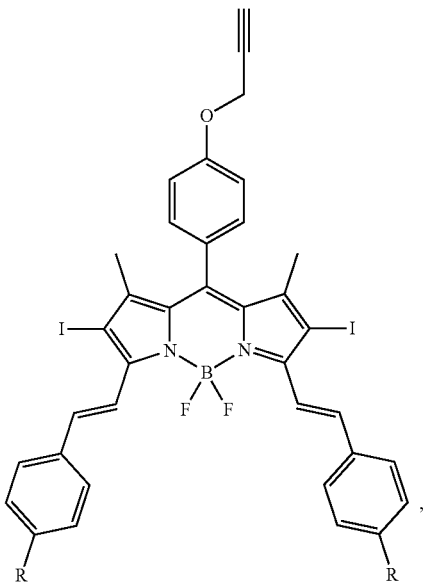

(III)

wherein R is

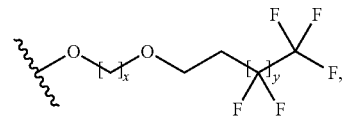

x+y=11, x and y are both a positive integer;
R¹ is

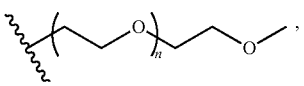

n=11-227, and n is a positive integer.

In an embodiment of the present invention, the solvent is selected from the group consisting of acetonitrile, toluene, benzene, N,N-dimethylformamide, dimethyl sulfoxide and any combination thereof.

In an embodiment of the present invention, in Step (1), the molar ratio of the compound of Formula (II),

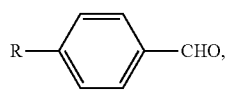

piperidine and acetic acid is 1:3-6:10-20:10-20.

In an embodiment of the present invention, in Step (1), the reaction temperature is 80-120° C.; and the reaction time is 12-48 h.

In an embodiment of the present invention, in Step (2), the molar ratio of the compound of Formula (III), azido functionalized polyethylene glycol, copper sulfate pentahydrate, and sodium ascorbate is 1:1-3:0.1-0.2:0.1-0.2.

In an embodiment of the present invention, in Step (2), the reaction temperature is 40-60° C.; and the reaction time is 12-24 h.

A third object of the present invention is to provide a nanomicelle solution, prepared by molecular self-assembly of the near-infrared nano-photosensitizer in water.

A fourth object of the present invention is to provide use of the near-infrared nano-photosensitizer or the nanomicelle in the preparation of drugs for the treatment of tumors.

Compared with the prior art, the technical solution of the present invention has the following advantages:
 (1) In the near-infrared nano-photosensitizer of the present invention, due to the particular performances of fluorine atoms, for example, small atomic radius, low polarizability, and high electronegativity of the fluorine atoms, the polyfluoroalkyl group or polyfluoroalkanes are caused to be neither hydrophilic nor lipophilic, so the polyfluoroalkyl group or polyfluoroalkanes tend to gather through fluorine-fluorine interaction, causing the formation of a third phase other than the aqueous phase and the oil phase, that is, the fluorine phase. The boron dipyrromethene core is modified by conjugation extension, achieving absorption and emission spectra close to the near-infrared region. A polyfluoroalkyl group and a polyethylene glycol group are introduced to the boron dipyrromethene structure to obtain an amphiphilic photosensitizer. By means of the strong fluorine-fluorine interaction between the polyfluoroalkyl group and the hydrophilic interaction of the polyethylene glycol group, a nano-photosensitive micelle with an ultra-low CMC value is ultimately constructed. Boron dipyrromethene is induced by fluorine-fluorine interaction to undergo J-aggregation, causing the maximum absorption peak to red-shift to the near-infrared region, which is beneficial to the deep phototherapy of tumors.
 (2) In the preparation process of the near-infrared nano-photosensitizer of the present invention, the conjugated system of boron dipyrromethene is extended by a condensation reaction, and a hydrophilic ethylene glycol chain is terminally introduced to solve the existing problems in the use of boron dipyrromethene compounds, and improve the water solubility. Furthermore, fluorine atoms are introduced through reaction to improve the driving force of molecular self-assembly, and the concept of multi-mode treatment combining photothermal and photodynamic therapy is introduced. The beneficial effects in increasing the yield of singlet oxygen, antitumor effect, and tumor targeting are confirmed by the results of cell experiments.
 (3) The near-infrared nano-photosensitizer of the present invention uses fluorine atoms to improve the efficient self-assembly of the photosensitizer and improve the tumor targeting. Moreover, the photophysical activity of BODIPY photosensitizer is regulated through fluorine atoms, causing the absorption peak of the new BODIPY photosensitizer to red shift to the near-infrared region, and increase the depth of treatment.

BRIEF DESCRIPTION OF THE DRAWINGS

To make the disclosure of the present invention more comprehensible, the present invention will be further described in detail by way of specific embodiments of the present invention with reference the accompanying drawings, in which.

DETAILED DESCRIPTION OF THE PREFERRED EMBODIMENTS

The present invention will be further described below with reference to the accompanying drawings and specific examples, so that those skilled in the art can better understand and implement the present invention; however, the present invention is not limited thereto.

In the present invention, unless otherwise indicated, group $R^1$ in the target compound is $(CH_2CH_2O)_nCH_2CH_2OCH_3$, and n is 113, that is, group $R^1$ is $(CH_2CH_2O)_{113}CH_2CH_2OCH_3$.

In the present invention, unless otherwise indicated, CHO-1 is

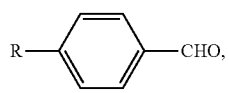

the substituent R in the examples is

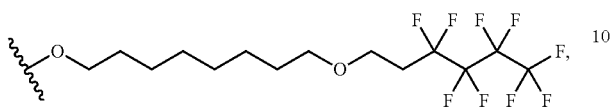

and the substituent R in the comparative examples is

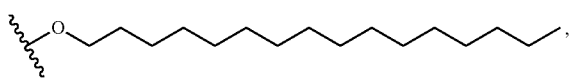 [SMILES: *OCCCCCCCCCCCCCCCC]

where ⌇ indicates only molecular connections.

EXAMPLE 1

Figure 1:
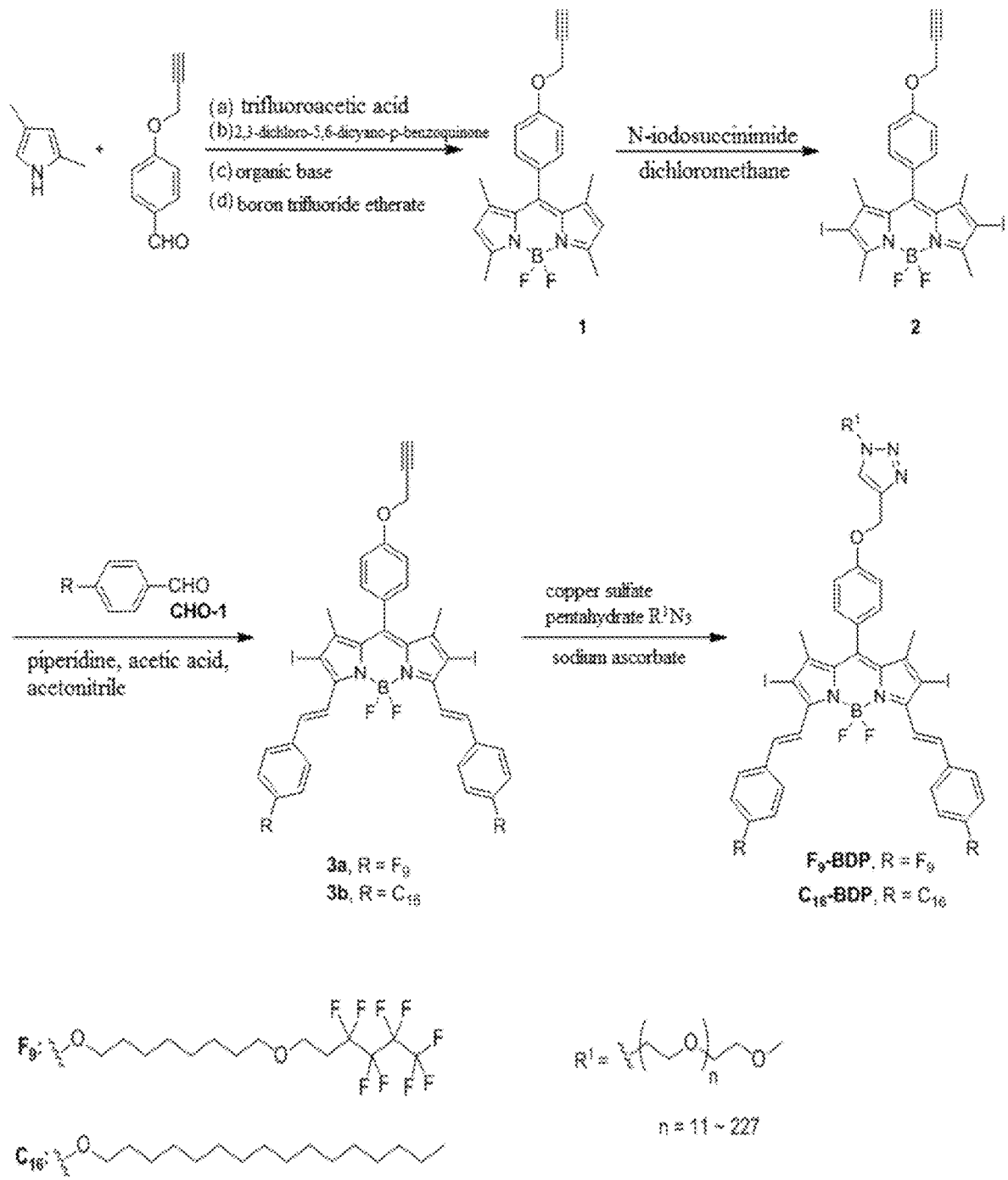
FIG. 1 shows a synthesis route for a target compound in the example and comparative example of the present invention, where 1, 2, 3a and 3b represent the products synthesized in each step of the reaction respectively, and $F_9$-BDP and $C_{16}$-BDP represent the target compounds synthesized respectively.

As shown in FIG. 1, a method for preparing a near-infrared nano-photosensitizer comprises specifically the following steps.
(1) Synthesis of Compound 1: Alkynyl-containing p-hydroxybenzaldehyde and 2,4-dimethylpyrrole were added to a reactor at a molar ratio of 1:1. Then tetrahydrofuran that was 100 times the weight of 2,4-dimethylpyrrole was added as a solvent, and 6-10 drops of trifluoroacetic acid was added as a catalyst, and stirred at for 24 h. Then, 2,3-dichloro-5,6-dicyano-p-benzoquinone at a molar ratio of 1.5:1 to 2,4-dimethylpyrrole was added to the reaction solution, and reacted with stirring at room temperature for 24 h. Finally, triethylamine that was 50 times the weight of 2,4-dimethylpyrrole was added, and boron trifluoride etherate that was 50 times the weight of 2,4-dimethylpyrrole was added dropwise in an ice-water bath and reacted overnight. After the reaction, the reaction solution was extracted with ethyl acetate and water, and concentrated by a rotary evaporator. The crude product was obtained after flash column chromatography, which was further subjected to column chromatography ($SiO_2$; eluent:petroleum ether/dichloromethane) to obtain Compound 1 (yield 70%).
(2) Synthesis of Compound 2: Compound 1 and N-iodosuccinimide were added to a reactor at a molar ratio of 1:2, and then 50 mL of dichloromethane was added as a solvent and reacted for 15 min. After the reaction was completed, the reaction solution was concentrated by a rotary evaporator, and then extracted. The organic layer was collected, dried, and concentrated to obtain a crude product. The crude product was separated by chromatography on silica gel column (eluent:petroleum ether-dichloromethane system), to obtain Compound 2 (yield 80%).
(3) Synthesis of Compound 3a: Compound 2 and CHO-1 were added to a reactor at a molar ratio of 1:4, and 10 mL of acetonitrile was added as a solvent. Finally, piperidine and acetic acid at a molar ratio of 15:15:1 to Compound 2 were heated to 100° C. under a nitrogen atmosphere and reacted under reflux for 12 h. After the reaction was completed, the reaction solution was concentrated, extracted, and subjected to column chromatography (petroleum ether: dichloromethane) to obtain Compound 3a, (yield 70%).
(4) Synthesis of Compound $F_9$-BDP: Compound 3a and azido functionalized polyethylene glycol ($R^1N_3$) were added to a reactor at a molar ratio of of (1:1.5). Copper sulfate pentahydrate and sodium ascorbate at a molar ratio of 0.1:0.1:1 to Compound 3a were added, and 5 mL of DMSO was added as a solvent. The reaction was continued under a nitrogen atmosphere at 55° C. for 24 h. After the reaction was completed, the reaction solution was concentrated, extracted, and subjected to column chromatography (methanol:dichloromethane) to obtain Compound $F_9$-BDP, (yield 50%).

EXAMPLE 2

A method for preparing a near-infrared nano-photosensitizer comprises specifically the following steps:
(1) Synthesis of Compound 1: Alkynyl-containing p-hydroxybenzaldehyde and 2,4-dimethylpyrrole were added to a reactor at a molar ratio of 1:3. Then tetrahydrofuran that was 50 times the weight of 2,4-dimethylpyrrole was added as a solvent, and 3-5 drops of trifluoroacetic acid was added as a catalyst, and stirred at for 24 h. Then, 2,3-dichloro-5,6-dicyano-p-benzoquinone at a molar ratio of 1:3 to 2,4-dimethylpyrrole was added to the reaction solution, and reacted with stirring at room temperature for 24 h. Finally, triethylamine that was 100 times the weight of 2,4-dimethylpyrrole was added, and boron trifluoride etherate that was 100 times the weight of 2,4-dimethylpyrrole was added dropwise in an ice-water bath and reacted overnight. After the reaction, the reaction solution was extracted with ethyl acetate and water, and concentrated by a rotary evaporator. The crude product was obtained after flash column chromatography, which was further subjected to column chromatography ($SiO_2$; eluent:petroleum ether/dichloromethane) to obtain Compound 1 (yield 60%).
(2) Synthesis of Compound 2: Compound 1 and N-iodosuccinimide were added to a reactor at a molar ratio of 1:3, and then dichloromethane that was 100 times the weight of Compound 1 was added as a solvent and reacted for 1 hr. After the reaction was completed, the reaction solution was concentrated by a rotary evaporator, and then extracted. The organic layer was collected, dried, and concentrated to obtain a crude product. The crude product was separated by chromatography on silica gel column (eluent:petroleum ether-dichloromethane system), to obtain Compound 2 (yield 70%).
(3) Synthesis of Compound 3a: Compound 2 and CHO-1 were added to a reactor at a molar ratio of 1:4, and toluene that was 50 times the weight of Compound 2 was used as a solvent. Finally, piperidine and acetic acid at a molar ratio of 20:20:1 to Compound 2 were heated to 80° C. under a nitrogen atmosphere and reacted under reflux for 24 h. After the reaction was completed, the reaction solution was concentrated, extracted, and subjected to column chromatography (petroleum ether: dichloromethane) to obtain Compound 3a (yield 50%).
(4) Synthesis of Compound $F_9$-BDP: Compound 3a and azido functionalized polyethylene glycol ($R^1N_3$) were added to a reactor at a molar ratio of (1:3). Copper sulfate pentahydrate and sodium ascorbate at a molar ratio of 0.2:0.2:1 to Compound 3a were added, and DMSO that was 20 times the weight of Compound 3a was added as a solvent. The reaction was continued under a nitrogen atmosphere at 40° C. for 24 h. After the reaction was completed, the reaction solution was concentrated, extracted, and subjected to column chromatography (methanol:dichloromethane) to obtain Compound $F_9$-BDP (yield 30%).

EXAMPLE 3

A method for preparing a near-infrared nano-photosensitizer comprises specifically the following steps:
(1) Synthesis of Compound 1: Alkynyl-containing p-hydroxybenzaldehyde and 2,4-dimethylpyrrole were added to a reactor at a molar ratio of 1:5. Then dichloromethane that was 30 times the weight of 2,4-dimethylpyrrole was added as a solvent, and 6-10 drops of trifluoroacetic acid was added as a catalyst, and stirred at for 48 h. Then, 2,3-dichloro-5,6-dicyano-p-benzoquinone at a molar ratio of 1:2 to 2,4-dimethylpyrrole was added to the reaction solution, and reacted with stirring at room temperature for 24 h. Finally, triethylamine that was 50 times the weight of 2,4-dimethylpyrrole was added, and boron trifluoride etherate that was 50 times the weight of 2,4-dimethylpyrrole was added dropwise in an ice-water bath and reacted overnight. After the reaction, the reaction solution was extracted with ethyl acetate and water, and concentrated by a rotary evaporator. The crude product was obtained after flash column chromatography, which was further subjected to column chromatography ($SiO_2$; eluent:petroleum ether/dichloromethane) to obtain Compound 1 yield 45%).
(2) Synthesis of Compound 2: Compound 1 and N-iodosuccinimide were added to a reactor at a molar ratio of 1:2, and then tetrahydrofuran that was 50 times the weight of Compound 1 was added as a solvent. The reaction was continued for 6 h. After the reaction was completed, the reaction solution was concentrated by a rotary evaporator, and then extracted. The organic layer was collected, dried, and concentrated to obtain a crude product. The crude product was separated by chromatography on silica gel column (eluent:petroleum ether-dichloromethane system), to obtain Compound 2 (yield 80%).
(3) Synthesis of Compound 3a: Compound 2 and CHO-1 were added to a reactor at a molar ratio of 1:6, and toluene that was 100 times the weight of Compound 2 was used as a solvent. Finally, piperidine and acetic acid at a molar ratio of 10:10:1 to Compound 2 were heated to 80° C. under a nitrogen atmosphere and reacted under reflux for 48 h. After the reaction was completed, the reaction solution was concentrated, extracted, and subjected to column chromatography (petroleum ether: dichloromethane) to obtain Compound 3a (yield 75%).
(4) Synthesis of Compound $F_9$-BDP: Compound 3a and azido functionalized polyethylene glycol ($R^1N_3$) were added to a reactor at a molar ratio of (1:2). Copper sulfate pentahydrate and sodium ascorbate at a molar ratio of 0.1:0.1:1 to Compound 3a were added, and DMSO that was 50 times the weight of Compound 3a was added as a solvent. The reaction was continued under a nitrogen atmosphere at 60° C. for 12 h. After the reaction was completed, the reaction solution was concentrated, extracted, and subjected to column chromatography (methanol:dichloromethane) to obtain Compound $F_9$-BDP (yield 45%).

EXAMPLE 4

A method for preparing a near-infrared nano-photosensitizer comprises specifically the following steps:
(1) Synthesis of Compound 1: Alkynyl-containing p-hydroxybenzaldehyde and 2,4-dimethylpyrrole were added to a reactor at a molar ratio of 1:2. Then dichloromethane that was 40 times the weight of 2,4-dimethylpyrrole was added as a solvent, and 5-8 drops of trifluoroacetic acid was added as a catalyst, and stirred at 20° C. for 24 h. Then, 2,3-dichloro-5,6-dicyano-p-benzoquinone at a molar ratio of 1:3 to 2,4-dimethylpyrrole was added to the reaction solution, and reacted with stirring at room temperature for 12 h. Finally, triethylamine that was 30 times the weight of 2,4-dimethylpyrrole was added, and boron trifluoride etherate that was 30 times the weight of 2,4-dimethylpyrrole was added dropwise in an ice-water bath and reacted overnight. After the reaction, the reaction solution was extracted with ethyl acetate and water, and concentrated by a rotary evaporator. The crude product was obtained after flash column chromatography, which was further subjected to column chromatography ($SiO_2$; eluent:petroleum ether/dichloromethane) to obtain Compound 1 (yield 25%).
(2) Synthesis of Compound 2: Compound 1 and N-iodosuccinimide were added to a reactor at a molar ratio of 1:3, and then tetrahydrofuran that was 30 times the weight of Compound 1 was added as a solvent. The reaction was continued for 12 h. After the reaction was completed, the reaction solution was concentrated by a rotary evaporator, and then extracted. The organic layer was collected, dried, and concentrated to obtain a crude product. The crude product was separated by chromatography on silica gel column (eluent:petroleum ether-dichloromethane system), to obtain Compound 2 (yield 45%).
(3) Synthesis of Compound 3a: Compound 2 and CHO-1 were added to a reactor at a molar ratio of 1:3, and benzene that was 50 times the weight of Compound 2 was used as a solvent. Finally, piperidine and acetic acid at a molar ratio of 10:10:1 to Compound 2 were heated to 120° C. under a nitrogen atmosphere and reacted under reflux for 24 h. After the reaction was completed, the reaction solution was concentrated, extracted, and subjected to column chromatography (petroleum ether: dichloromethane) to obtain Compound 3a, (yield 60%).
(4) Synthesis of Compound $F_9$-BDP: Compound 3a and azido functionalized polyethylene glycol ($R^1N_3$) were added to a reactor at a molar ratio of (1:1). Copper sulfate pentahydrate and sodium ascorbate at a molar ratio of 0.1:0.1:1 to Compound 3a were added, and DMF that was 50 times the weight of Compound 3a was added as a solvent. The reaction was continued under a nitrogen atmosphere at 40° C. for 24 h. After the reaction was completed, the reaction solution was concentrated, extracted, and subjected to column chromatography (methanol:dichloromethane) to obtain Compound $F_9$-BDP, (yield 48%).

EXAMPLE 5

A method for preparing a near-infrared nano-photosensitizer comprises specifically the following steps:

(1) Synthesis of Compound 1: Alkynyl-containing p-hydroxybenzaldehyde and 2,4-dimethylpyrrole were added to a reactor at a molar ratio of 1:3. Then tetrahydrofuran that was 80 times the weight of 2,4-dimethylpyrrole was added as a solvent, and 10 drops of trifluoroacetic acid was added as a catalyst, and stirred at for 12 h. Then, 2,3-dichloro-5,6-dicyano-p-benzoquinone at a molar ratio of 1:5 to 2,4-dimethylpyrrole was added to the reaction solution, and reacted with stirring at room temperature for 24 h. Finally, triethylamine that was 50 times the weight of 2,4-dimethylpyrrole was added, and boron trifluoride etherate that was 50 times the weight of 2,4-dimethylpyrrole was added dropwise in an ice-water bath and reacted overnight. After the reaction, the reaction solution was extracted with ethyl acetate and water, and concentrated by a rotary evaporator. The crude product was obtained after flash column chromatography, which was further subjected to column chromatography ($SiO_2$; eluent:petroleum ether/dichloromethane) to obtain Compound 1 (yield 33%).

(2) Synthesis of Compound 2: Compound 1 and N-iodosuccinimide were added to a reactor at a molar ratio of 1:5, and then tetrahydrofuran that was 50 times the weight of Compound 1 was added as a solvent. The reaction was continued for 24 h. After the reaction was completed, the reaction solution was concentrated by a rotary evaporator, and then extracted. The organic layer was collected, dried, and concentrated to obtain a crude product. The crude product was separated by chromatography on silica gel column (eluent:petroleum ether-dichloromethane system), to obtain Compound 2 (yield 90%).

(3) Synthesis of Compound 3a: Compound 2 and CHO-1 were added to a reactor at a molar ratio of 1:6, and toluene that was 100 times the weight of Compound 2 was used as a solvent. Finally, piperidine and acetic acid at a molar ratio of 20:20:1 to Compound 2 were heated to 120° C. under a nitrogen atmosphere and reacted under reflux for 24 h. After the reaction was completed, the reaction solution was concentrated, extracted, and subjected to column chromatography (petroleum ether: dichloromethane) to obtain Compound 3a (yield 56%).

(4) Synthesis of Compound $F_9$-BDP: Compound 3a and azido functionalized polyethylene glycol ($R^1N_3$) were added to a reactor at a molar ratio of (1:1.5). Copper sulfate pentahydrate and sodium ascorbate at a molar ratio of 0.1:0.1:1 to Compound 3a were added, and DMF that was 50 times the weight of Compound 3a was added as a solvent. The reaction was continued under a nitrogen atmosphere at 60° C. for 24 h. After the reaction was completed, the reaction solution was concentrated, extracted, and subjected to column chromatography (methanol:dichloromethane) to obtain Compound $F_9$-BDP, yield 62%).

COMPARATIVE EXAMPLE 1

As shown in FIG. 1, a method for preparing a nano-photosensitizer comprises specifically the following steps:
(1) Synthesis of Compound 1: Alkynyl-containing p-hydroxybenzaldehyde and 2,4-dimethylpyrrole were added to a reactor at a molar ratio of 1:1. Then tetrahydrofuran that was 100 times the weight of 2,4-dimethylpyrrole was added as a solvent, and 6-10 drops of trifluoroacetic acid was added as a catalyst, and stirred at for 24 h. Then, 2,3-dichloro-5,6-dicyano-p-benzoquinone at a molar ratio of 1:1.5 to 2,4-dimethylpyrrole was added to the reaction solution, and reacted with stirring at room temperature for 24 h. Finally, triethylamine that was 50 times the weight of 2,4-dimethylpyrrole was added, and boron trifluoride etherate that was 50 times the weight of 2,4-dimethylpyrrole was added dropwise in an ice-water bath and reacted overnight. After the reaction, the reaction solution was extracted with ethyl acetate and water, and concentrated by a rotary evaporator. The crude product was obtained after flash column chromatography, which was further subjected to column chromatography ($SiO_2$; eluent:petroleum ether/dichloromethane) to obtain Compound 1 (yield 70%).

(2) Synthesis of Compound 2: Compound 1 and N-iodosuccinimide were added to a reactor at a molar ratio of 1:2, and then 50 mL of dichloromethane was added as a solvent and reacted for 15 min. After the reaction was completed, the reaction solution was concentrated by a rotary evaporator, and then extracted. The organic layer was collected, dried, and concentrated to obtain a crude product. The crude product was separated by chromatography on silica gel column (eluent:petroleum ether-dichloromethane system), to obtain Compound 2 (yield 80%).

(3) Synthesis of Compound 3b: Compound 2 and CHO-1 were added to a reactor at a molar ratio of 1:4, and 10 mL of acetonitrile was added as a solvent. Finally, piperidine and acetic acid at a molar ratio of 15:15:1 to Compound 2 were heated to 100° C. under a nitrogen atmosphere and reacted under reflux for 12 h. After the reaction was completed, the reaction solution was concentrated, extracted, and subjected to column chromatography (petroleum ether:dichloromethane) to obtain Compound 3b (yield 65%).

(4) Synthesis of Compound $C_{16}$-BDP: Compound 3b and azido functionalized polyethylene glycol ($R^1N_3$) were added to a reactor at a molar ratio of (1:1.5). Copper sulfate pentahydrate and sodium ascorbate at a molar ratio of 0.1:0.1:1 to Compound 3b were added, and 5 mL of DMSO was added as a solvent. The reaction was continued under a nitrogen atmosphere at 55° C. for 24 h. After the reaction was completed, the reaction solution was concentrated, extracted, and subjected to column chromatography (methanol:dichloromethane) to obtain Compound $C_{16}$-BDP (yield 50%).

TEST EXAMPLE 1

Figure 2:
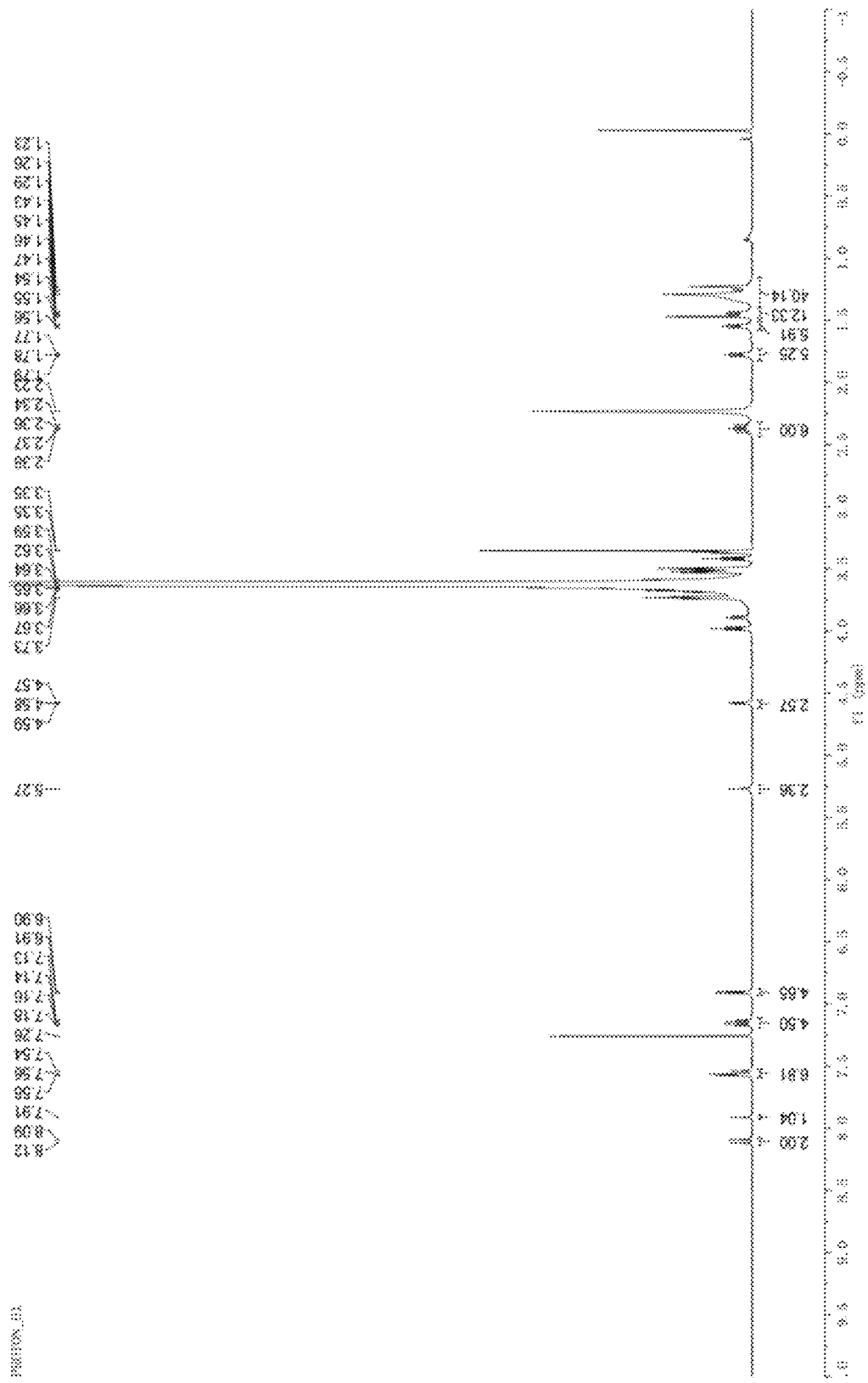
FIG. 2 shows a $^1$H NMR spectrum of Compound $F_9$-BDP in Test Example 1 of the present invention.
Figure 3:
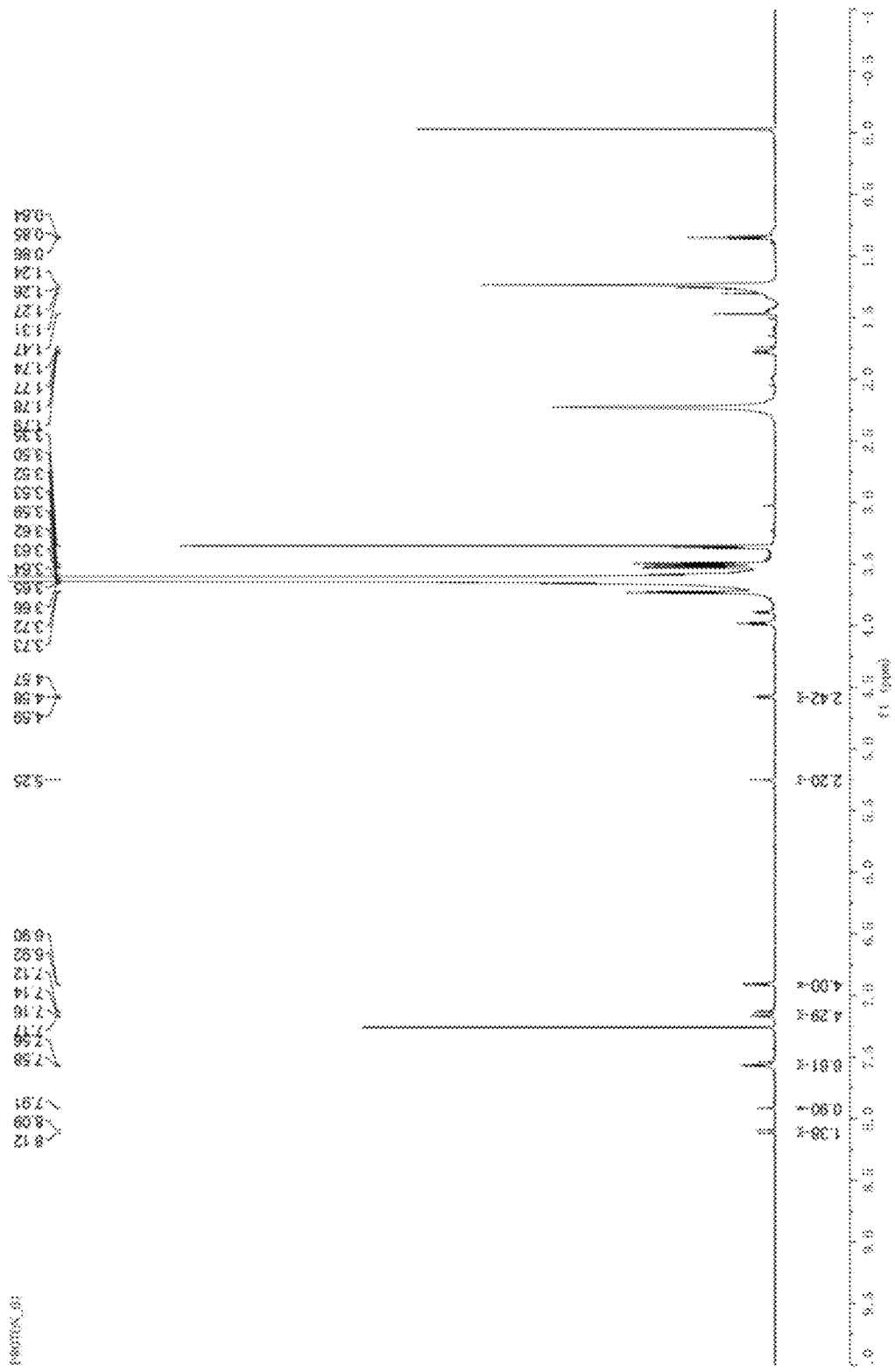
FIG. 3 shows a $^1$H NMR spectrum of Compound $C_{16}$-BDP in Test Example 1 of the present invention.

The target product $F_9$-BDP in Example 1 and the $C_{16}$-BDP prepared in Comparative Example 1 were identified by NMR.
As shown in FIGS. 2-3, the target product is successfully synthesized.

TEST EXAMPLE 2

The nanomicelles of nano-photosensitizer $C_{16}$-BDP-NPs or $F_9$-BDP-NPs were characterized and investigated by transmission electron microscopy.
A small amount of Compound $C_{16}$-BDP in Example 1 or Compound $F_9$-BDP in Comparative Example was taken by thin film dispersion. $C_{16}$-BDP or $F_9$-BDP was dissolved in an organic reagent (such as dichloromethane or acetone), and dried by rotary evaporation. An appropriate amount of deionized water was added with ultrasonicating, and ultrasonicated for further 10-60 min, to prepare nanomicelles of nano-photosensitizer $C_{16}$-BDP-NPs or $F_9$-BDP-NPs.

Figure 4:
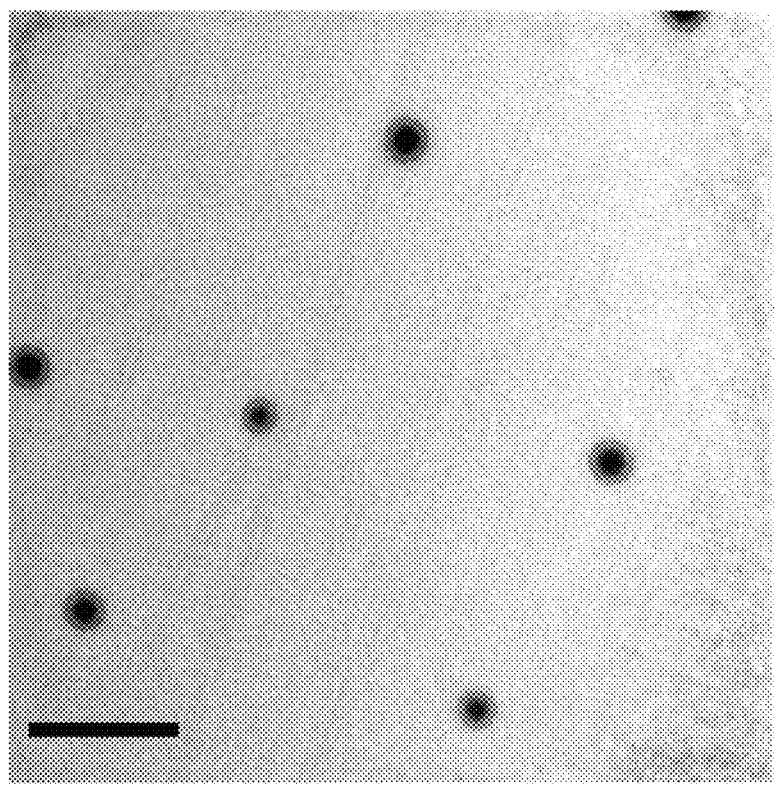
FIG. 4 shows the particle size distribution of the nanomicelles of the photosensitizer $F_9$-BDP-NPs in Test Example 2 of the present invention (scale bar=500 nm).
Figure 5:
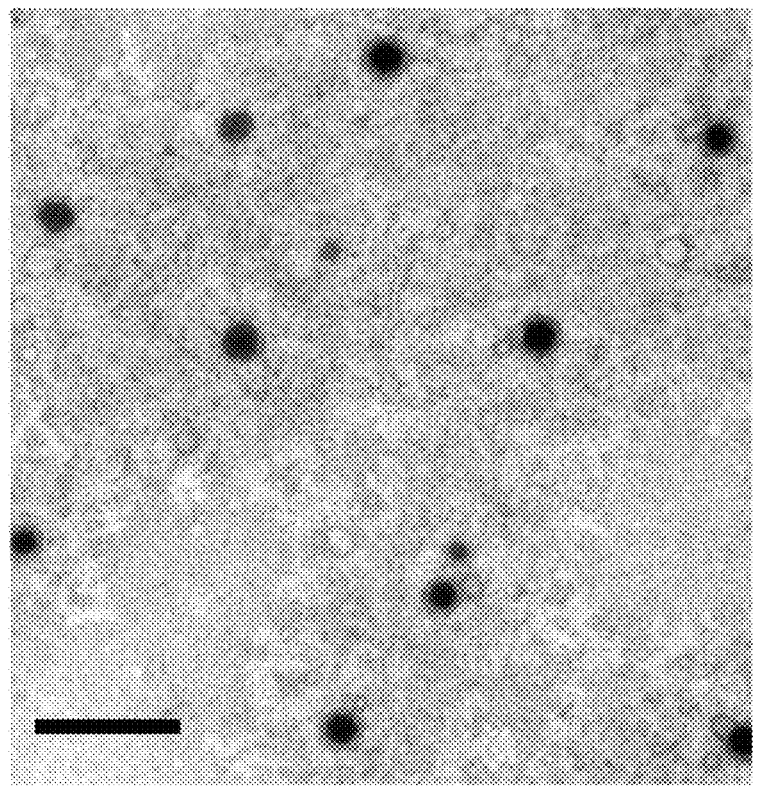
FIG. 5 shows the particle size distribution of the nanomicelles of the photosensitizer $C_{16}$-BDP-NPs in Test Example 2 of the present invention (scale bar=500 nm).

A nanomicelle solution of equal concentration was prepared, dripped onto a copper grid, volatilized to dryness, and photographed under a transmission electron microscope. As shown in FIGS. 4-5, the nano-photosensitizer $C_{16}$-BDP-NPs or $F_9$-BDP-NPs is shown to have a uniform nano-size.

TEST EXAMPLE 3

The prepared nanomicelles of $C_{16}$-BDP-NPs or $F_9$-BDP-NPs were determined by spectroscopy.

Figure 6:
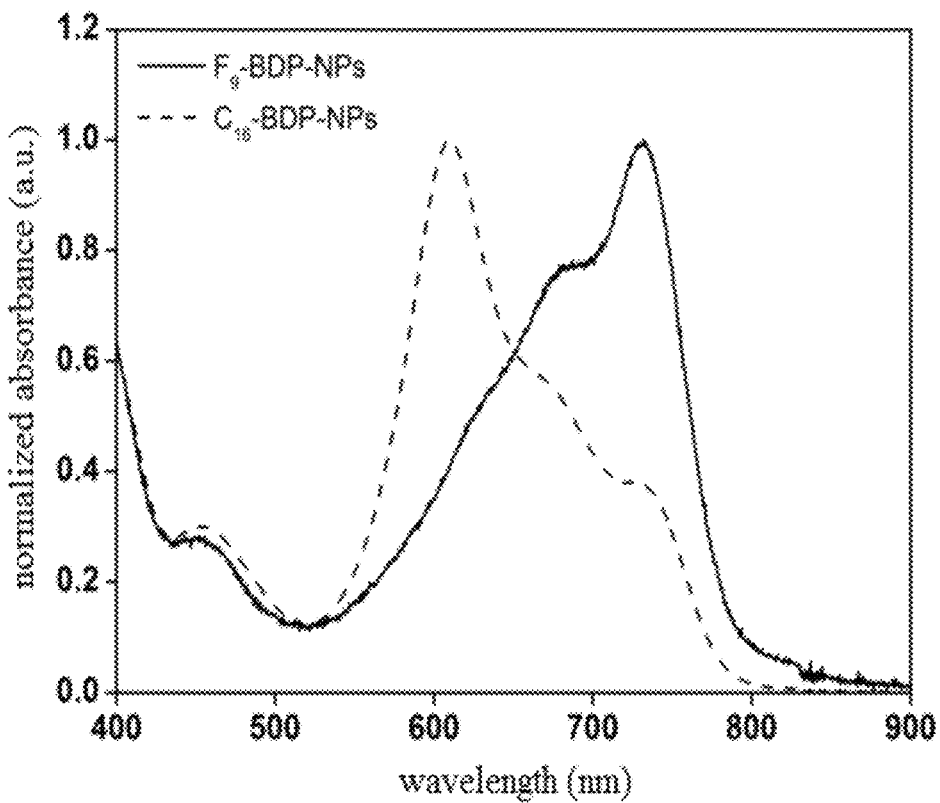
FIG. 6 shows the ultraviolet-visible absorption spectra of the nano-micelles of $F_9$-BDP-NPs and $C_{16}$-BDP-NPs in Test Example 3 of the present invention.
Figure 7:
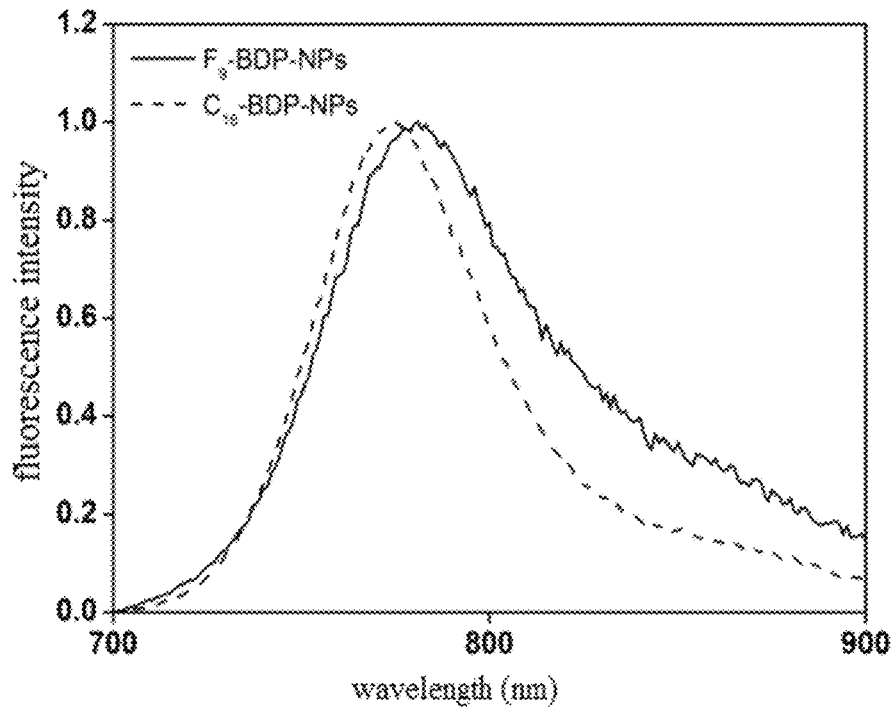
FIG. 7 shows the fluorescence emission spectra of the nano-micelles of $F_9$-BDP-NPs and $C_{16}$-BDP-NPs in Test Example 3 of the present invention.

As shown in FIGS. 6-7, the maximum absorption wavelength of $C_{16}$-BDP-NPs nanomicelle is about 600 nm, and the absorption wavelength of $C_{16}$-BDP-NPs is blue-shifted. The maximum absorption wavelength of $F_9$-BDP-NPs nanomicelle is about 720 nm, and the absorption wavelength of $F_9$-BDP-NPs nanomicelle is red-shifted to the near-infrared region. Moreover, a high-efficiency near-infrared BODIPY photosensitizer is preliminarily confirmed to be successfully synthesized by the fluorescence intensity, and the fluorescence intensity of $F_9$-BDP-NPs nanomicelles is significantly higher than that of $C_{16}$-BDP-NPs nanomicelle.

TEST EXAMPLE 4

The critical micelle concentration (CMC) of the prepared $C_{16}$-BDP-NPs or $F_9$-BDP-NPs nanomicelle solution with different concentrations was determined.

Figure 8:
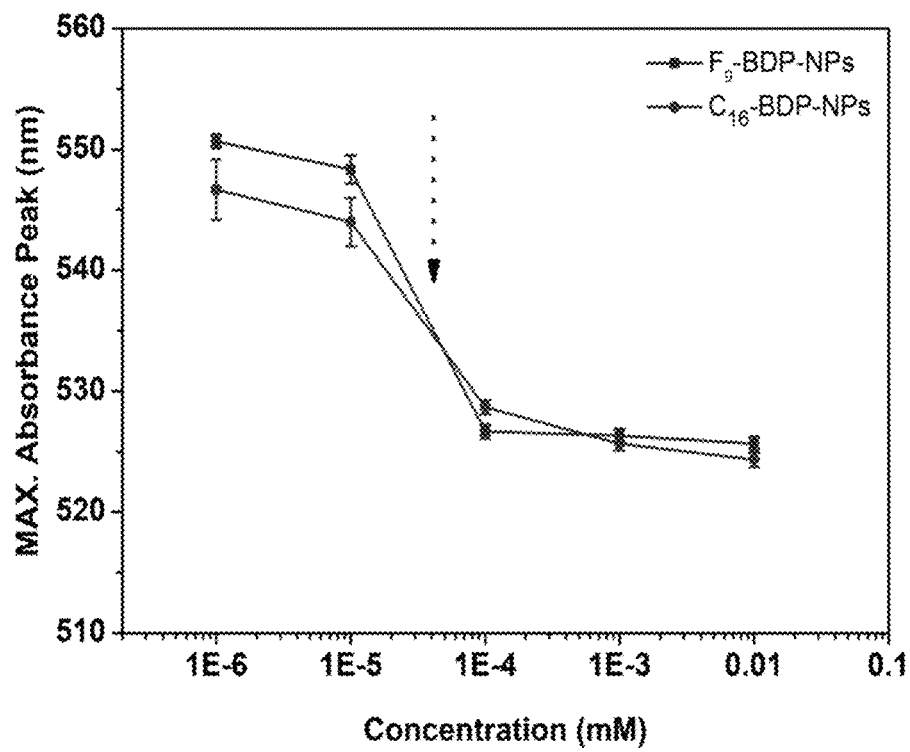
FIG. 8 shows the critical micelle concentration of the nano-micelles of $F_9$-BDP-NPs and $C_{16}$-BDP-NPs in Test Example 4 of the present invention.

Because a critical micelle concentration (CMC) of below $1^{-3}$ mM is difficult to be measured by the traditional pyrene test method, the CMC values of $F_9$-BDP-NPs and $C_{16}$-BDP-NPs nanomicelles were tested by the nano-gold method. The changes of the UV-Vis absorption spectrum of the compound at various concentrations were observed. The results are shown in FIG. 8. The CMC values of $F_9$-BDP-NPs and $C_{16}$-BDP-NPs are respectively $7.4 \times 10^{-5}$ mM and $1.5 \times 10^{-4}$ mM, and the critical micelle value of $F_9$-BDP-NPs is much lower than those of 2-IBMs ($10^{-3}$ mM) and traditional polymer micelles (>$10^{-3}$ mM) in Patent No. CN109078185A.

It can be seen that the $F_9$-BDP-NPs nanomicelle solution has a very low CMC value, and can maintain a nanomicelle state at a low concentration.

TEST EXAMPLE 5

The singlet oxygen yield of the prepared $C_{16}$-BDP-NPs or $F_9$-BDP-NPs nanomicelles was investigated.

Figure 9:
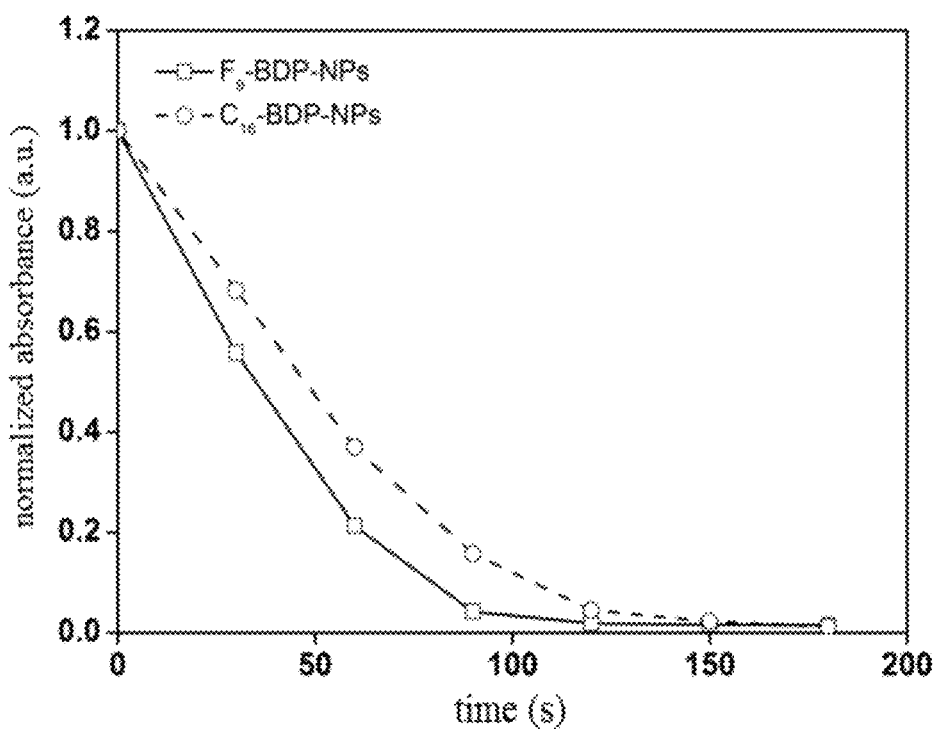
FIG. 9 shows DPBF quenched in the $F_9$-BDP-NPs and $C_{16}$-BDP-NPs solutions under irradiation in Test Example 5 of the present invention.

A nanomicelle solution of equal concentration was prepared, which contained equimolar 1,3-diphenylisobenzofuran. The solution was irradiated for 180 s using a halogen lamp (>660 nm, 0.1 W/cm²) as an excitation light source in the irradiation experiment. The UV-Vis absorption spectrum of the solution was measured every 30 s, and the changes in the UV-Vis absorption of the solution was observed at 415 nm and plotted to obtain a broken-line diagram of singlet oxygen yield. As shown in FIG. 9, $C_{16}$-BDP-NPs or $F_9$-BDP-NPs nanomicelles have higher yields of singlet oxygen, especially $F_9$-BDP-NPs nanomicelles. Therefore, $F_9$-BDP-NPs nanomicelles provide a basis for better realization of photodynamic therapy.

TEST EXAMPLE 6

A cytotoxicity experiment was performed using the prepared $C_{16}$-BDP-NPs or $F_9$-BDP-NPs nanomicelles.

Figure 10:
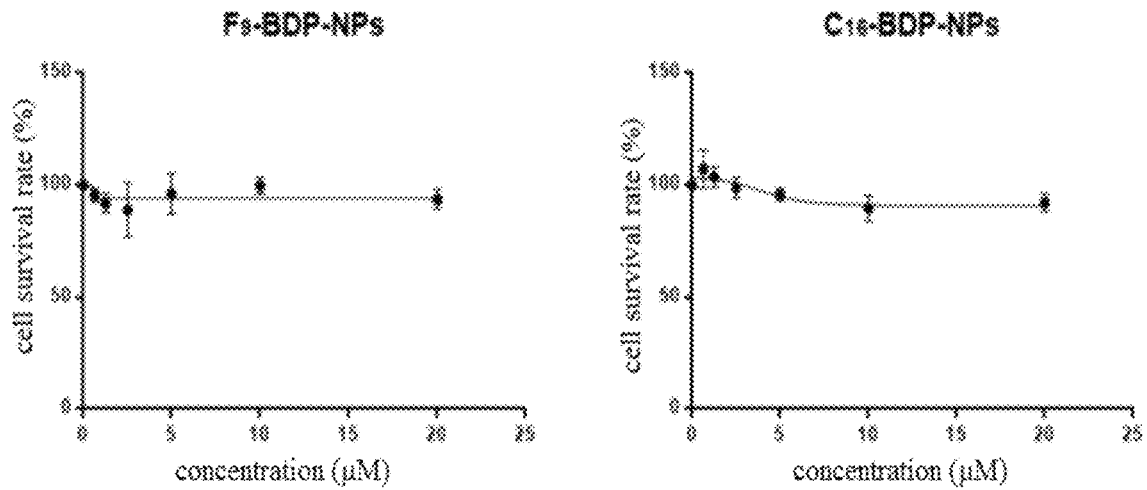
FIG. 10 shows the cytotoxicity of $F_9$-BDP-NPs and $C_{16}$-BDP-NPs without irradiation in Test Example 6 of the present invention.
Figure 11:
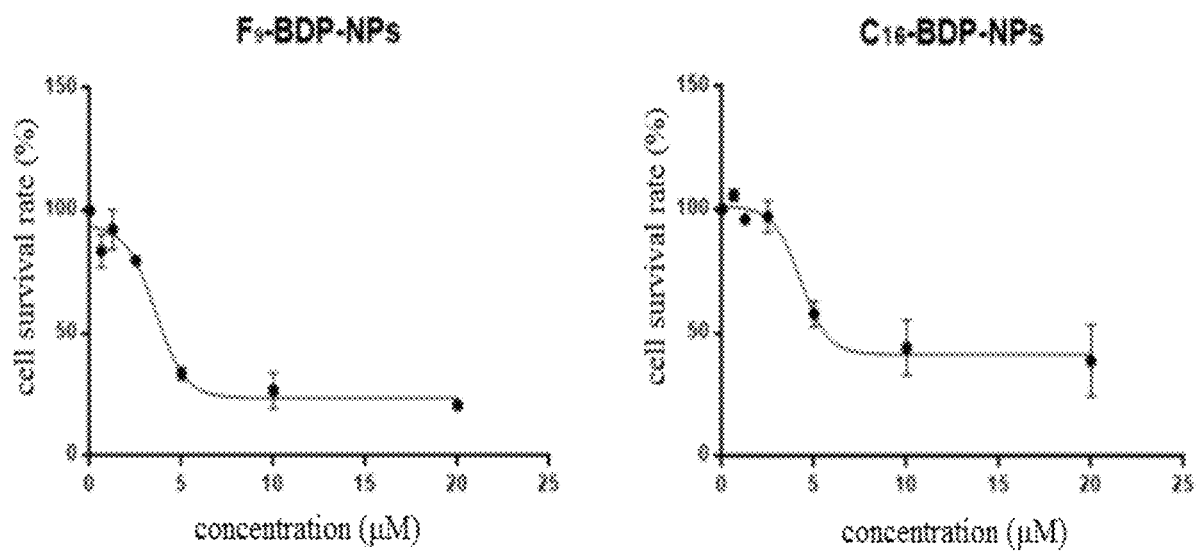
FIG. 11 shows the cytotoxicity of $F_9$-BDP-NPs and $C_{16}$-BDP-NPs under irradiation (>660 nm halogen lamp, 100 mW/cm$^2$), in Test Example 6 of the present invention.

4T1 cells in the logarithmic growth phase were taken and plated in a 96-well plate in 100 μL/well at a seeding density of $6 \times 10^3$/mL. The cells were incubated in a cell incubator at a constant temperature for 12 h. After confirming that the cells were attached, the culture medium was poured off. The cells were washed 1-2 times with a phosphate buffer, a $C_{16}$-BDP-NPs or $F_9$-BDP-NPs nanomicelle solution prepared in the culture medium was added in 100 μL/well. The concentration gradients in the irradiation group were set to 0.625, 1.25, 2.5, 5.0, 10, and 20 μM, and 4 replicate wells were set for each concentration. The concentration gradients in the non-irradiation group were also set to 0.625, 1.25, 2.5, 5.0, 10, and 20 μM, and 4 replicate wells were set for each concentration. After 24 h of incubation in the incubator, the culture medium was changed. The cells in the irradiation group were irradiated for 30 min at 0.1 W/cm², and then incubated in the cell incubator for another 12 h. A solution of MTT in PBS (5 mg/mL, 20 μL) was added and the culture medium was discarded after 4 h. DMSO was added (150 μL), and shaken for 10 min. The absorbance was measured at 490 nm on a microplate reader. As shown in FIGS. 10 to 11, $F_9$-BDP-NPs nanomicelles have a lower $IC_{50}$ value under light, and a relatively low toxicity in the dark. This indicates that only laser of particular wavelength can cause the toxic effect of the drug.

TEST EXAMPLE 7

A tissue distribution of the prepared $C_{16}$-BDP-NPs or $F_9$-BDP-NPs nanomicelles in mice was tested. Specifically (1) Establishment of tumor-bearing mouse model: BALB/c female mice weighing 20 g were selected in advance, and 4T1 cells in good growth state were collected. Each mouse was inoculated with $10^7$ cells in a volume of 50 μL, by subcutaneously injecting into the dorsal side of mice.

(2) Radioactive labeling of nanomicelles: 500 L of $C_{16}$-BDP-NPs or $F_9$-BDP-NPs nanomicelle solution (400 μM) was respectively added to a 2 mL EP tube. 5 mg of Iodogen was additionally weighed, added to a 2 mL EP tube, and dissolved by adding 1 mL of trichloromethane. After dissolution, the solution was blow dried with nitrogen, to spread it evenly at the bottom of the tube. Subsequently, 1 mCi $^{125}$I was taken from a lead can and added to the above-mentioned EP tube. $C_{16}$-BDP-NPs or $F_9$-BDP-NPs nanomicelles were added, and shaken on a shaker at room temperature for 20 min. The reaction was terminated after 20 min. The solution in the EP tube was transferred to an ultrafiltration tube for ultrafiltration and centrifugation (3500 rpm, 15 min). After centrifugation, the radioactivity in the upper and lower tube of the ultrafiltration tube was tested using a radioactivity meter. Three times of centrifugation were carried out.

Figure 12:
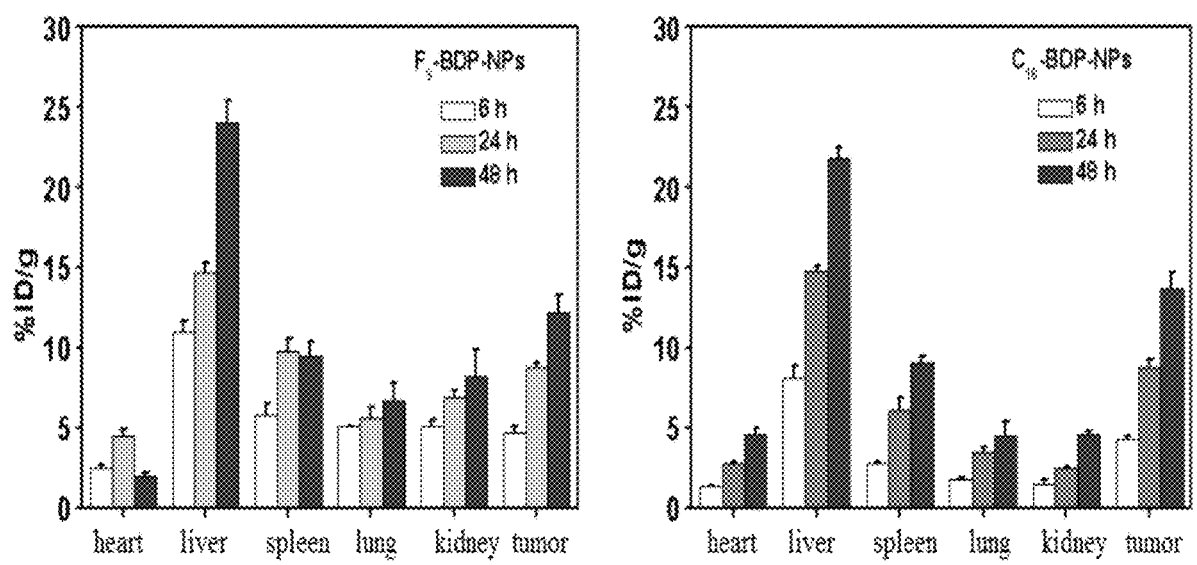
FIG. 12 shows the tissue distribution at various time points after tail vein injection of F9-BDP-NPs and C16-BDP-NPs in Test Example 7 of the present invention.

(3) The established female BALB/c tumor-bearing mice (3 animals in each group) were injected with the radiolabeled nanomicelles (400 μM, having a nuclide content of 20 μCi) at the tail vein. The dosing schedule was set. After that, the mice were sacrificed, and the tissue was removed. Each tissue was weighed, and added to a FACS tube. The radioactive content in the tissue was tested by a gamma immunocounter, and quantified by calculation. As shown in FIG. 12, the drug containing $F_9$-BDP-NPs nanomicelles has good tumor targeting in mice.

Accordingly, the $F_9$-BDP-NPs nanomicelle solution has more excellent properties and better application prospects.

Obviously, the above-described embodiments are merely examples provided for clarity of description, and are not intended to limit the implementations of the present invention. Other variations or changes can be made by those skilled in the art based on the above description. The embodiments are not exhaustive herein. Obvious variations or changes derived therefrom also fall within the protection scope of the present invention.

What is claimed is:

1. A near-infrared nano-photosensitizer, having a structure of Formula (I):

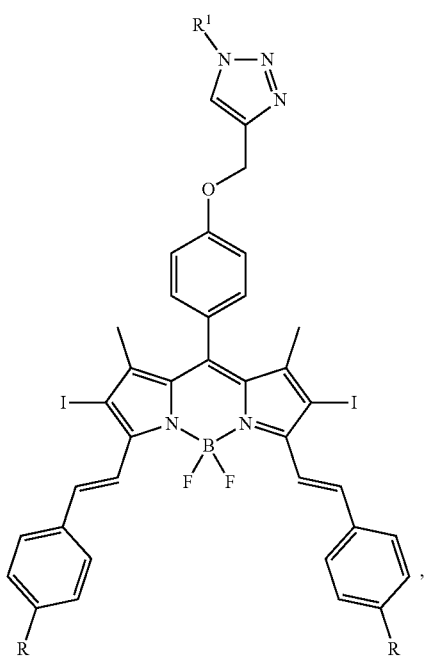

wherein R is

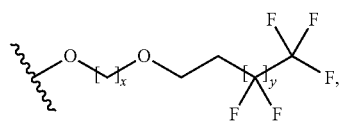

x+y=11, x and y are both a positive integer;

R¹ is

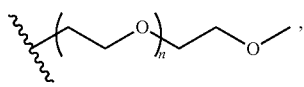

n=11-221, and n is a positive integer.

2. The near-infrared nano-photosensitizer according to claim 1, wherein y is 3, 5 or 7.

3. A method for preparing a near-infrared nano-photosensitizer according to claim 1, comprising steps of:

(1) reacting a compound of Formula (II) with

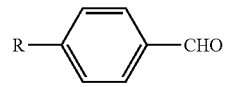

in the presence of acetic acid and piperidine in a solvent, to obtain a compound of Formula (III); and (2) reacting the compound of Formula (III) obtained in Step (1) with azido functionalized polyethylene glycol in the presence of copper sulfate pentahydrate and sodium ascorbate in a solvent, to obtain a compound of Formula (I), wherein the structures of Formulas (I), (II) and (III) are shown below:

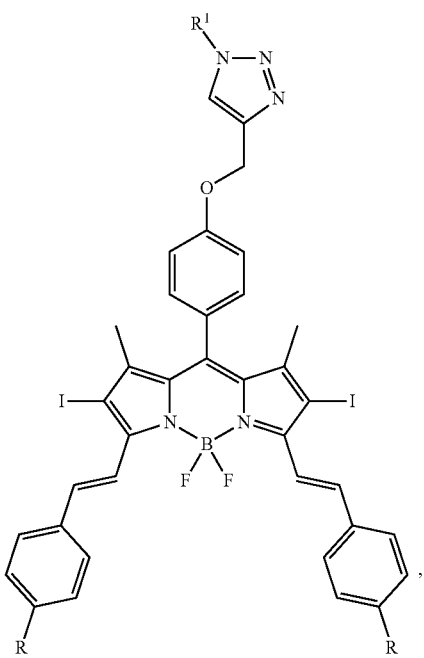

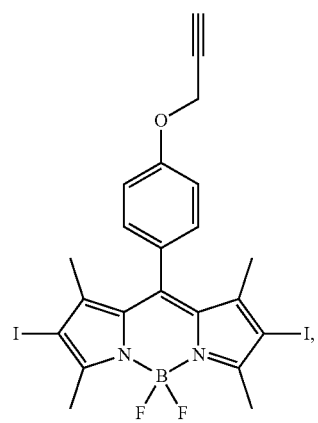

-continued (III)

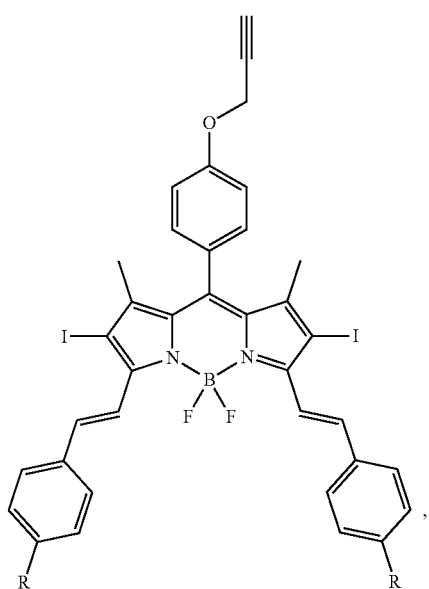

wherein R is

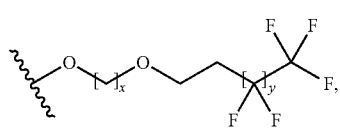

x+y=11, x and y are both a positive integer;
R¹ is

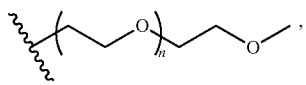

n=11-227, and n is a positive integer.

4. The method for preparing a near-infrared nano-photosensitizer according to claim 3, wherein the solvent is selected from the group consisting of acetonitrile, toluene, benzene, N,N-dimethylformamide, dimethyl sulfoxide and any combination thereof.

5. The method for preparing a near-infrared nano-photosensitizer according to claim 3, wherein in Step (1), the molar ratio of the compound of Formula (II),

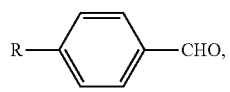

piperidine and acetic acid is 1:3-6:10-20:10-20.

6. The method for preparing a near-infrared nano-photosensitizer according to claim 3, wherein in Step (1), the reaction temperature is 80-120° C.; and the reaction time is 12-48 h.

7. The method for preparing a near-infrared nano-photosensitizer according to claim 3, wherein in Step (2), the molar ratio of the compound of Formula (III), azido functionalized polyethylene glycol, copper sulfate pentahydrate, and sodium ascorbate is 1:1-3:0.1-0.2:0.1-0.2.

8. The method for preparing a near-infrared nano-photosensitizer according to claim 3, wherein in Step (2), the reaction temperature is 40-60° C.; and the reaction time is 12-24 h.

9. A nanomicelle solution comprising a near-infrared nano-photosensitizer according to claim 1 in water.

10. An anti-tumor composition comprising a near-infrared nano-photosensitizer according to claim 1 in the preparation of drugs for the treatment of tumors.

* * * * *